(12) United States Patent
Becker

(10) Patent No.: US 8,710,241 B2
(45) Date of Patent: Apr. 29, 2014

(54) CRYSTALLINE FORM OF ZOFENOPRIL CALCIUM

(75) Inventor: Axel Becker, Hertfordshire (GB)

(73) Assignee: Generics [UK]Limited, Hertfordshire (GB)

( * ) Notice: Subject to any disclaimer, the term of this patent is extended or adjusted under 35 U.S.C. 154(b) by 644 days.

(21) Appl. No.: 12/671,328

(22) PCT Filed: Aug. 8, 2008

(86) PCT No.: PCT/GB2008/050683
§ 371 (c)(1),
(2), (4) Date: Aug. 5, 2010

(87) PCT Pub. No.: WO2009/022168
PCT Pub. Date: Feb. 19, 2009

(65) Prior Publication Data
US 2011/0098334 A1    Apr. 28, 2011

(30) Foreign Application Priority Data
Aug. 10, 2007 (GB) .................. 0715626.8

(51) Int. Cl.
*A61K 31/40* (2006.01)
*C07D 207/04* (2006.01)

(52) U.S. Cl.
CPC ............ *C07D 207/04* (2013.01); *A61K 31/40* (2013.01)
USPC ............................ 548/450; 548/540; 514/423

(58) Field of Classification Search
CPC ................................ C07D 207/04; A61K 31/40
USPC ............................................... 548/450
See application file for complete search history.

(56) References Cited

U.S. PATENT DOCUMENTS

| 4,316,906 A | 2/1982 | Ondetti et al. |
| 6,515,012 B2 | 2/2003 | Giorgi et al. |
| 6,521,760 B1 | 2/2003 | Giorgi et al. |
| 2002/0156293 A1 | 10/2002 | Giorgi et al. |
| 2005/0209288 A1 | 9/2005 | Grogan et al. |

FOREIGN PATENT DOCUMENTS

| JP | 5527199 | 2/1980 |
| JP | H01287069 | 11/1989 |
| JP | 2002522417 | 7/2002 |
| WO | WO 00/07984 | 2/2000 |
| WO | WO 2007/003963 | 1/2007 |
| WO | WO 2007/138352 | 12/2007 |

OTHER PUBLICATIONS

International Search Report PCT/GB2008/050683dated Nov. 13, 2008 (4 pgs.).
Joel Bernstein, "Poylmorphism in Molecular Crystals", Department of Chemistry, Table. 4.6, Clarendon Press, Oxford, 2002, pp. 3.
Ruben Lozano et al., "Temperature, pH and agitation rate as dissolution test discriminators of zofenopril calcium tablets", Journal of Pharmaceutical and Biomedical Analysis, 1994, vol. 12(2), pp. 173-177.
Chemical Abstracts Accession No. 1982:218225, pp. 2, 1982
Hurst et al., Analytica Chimica Acta., 1997, vol. 337, pp. 233-252.
Brittain (Ed.), Polymorphism in Pharmaceutical Solids, 1999.
Morissette et al., Advanced Drug Delivery Reviews, 2004, vol. 56, pp. 275-300.
Campbell Roberts et al., Journal of Pharmaceutical and Biomedical Analysis, 2002, vol. 28, pp. 1149-1159.
Tiwari et al., Journal of Pharmaceutical and Biomedical Analysis, 2007, vol. 43, pp. 865-872.
Chen et al., Journal of Pharmaceutical Sciences, 1999, vol. 88(11), pp. 1191-1200.
U.S. Pharmacopia #23, National Formulary #18, 1995, pp. 1843-1844.
Caira, Topics in Current Chemistry, vol. 198, 1998, pp. 163-208.
Ganapathy et al., Journal of the American Chemical Society, 2002, vol. 124, pp. 7821-7828.
http:www.convachem.com/product/81938-43-4.html © Convachem web listing for Zofenopril Calcium, Mar. 5, 2008.

*Primary Examiner* — Jeffrey S. Lundgren
*Assistant Examiner* — Meghan Finn
(74) *Attorney, Agent, or Firm* — Fulbright & Jaworski, LLP; Scott D. Rothenberger

(57) ABSTRACT

The present invention relates to a novel anhydrous crystalline form of zofenopril calcium of formula (I), chemically known as (4S)-1-[(2S)-3-(benzoylthio)-2-methylpropionyl]-4-(phenylthio)-L-proline calcium salt or hemi-calcium salt. The present invention further relates to a process for the preparation of the new crystalline form of zofenopril calcium, its use in pharmaceutical compositions and the use of the new crystalline form and compositions in the treatment of hypertension and various other diseases.

Formula (I)

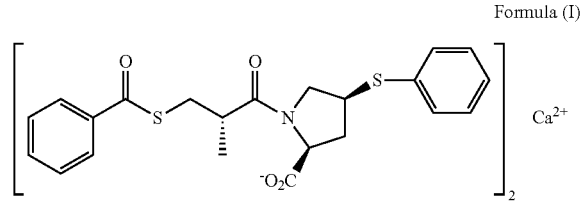

16 Claims, 6 Drawing Sheets

CRYSTALLINE FORM OF ZOFENOPRIL CALCIUM

CROSS-REFERENCE TO RELATED APPLICATION(S)

Figure 1:
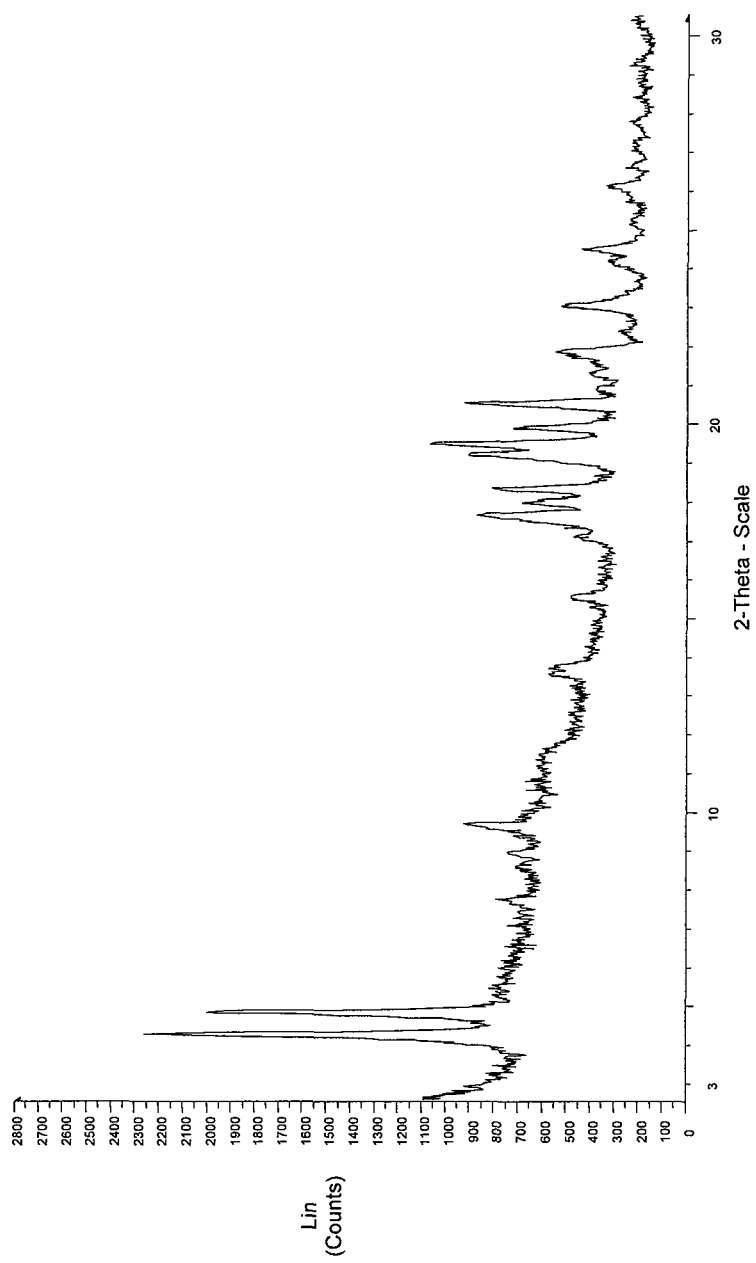

This application is a Section 371 National Stage Application of International No. PCT/GB2008/050683, filed 8 Aug. 2008 and published as WO 2009/022168 A1 on 8 Aug. 2008, which claims priority from the Great Britain Application 0715626.8, filed 10 Aug. 2007, the contents of which are incorporated herein in their entirety for all purposes.

TECHNICAL FIELD OF THE INVENTION

The present invention relates to a novel anhydrous crystalline form of zofenopril calcium of formula (I), chemically known as (4S)-1-[(2S)-3-(benzoylthio)-2-methylpropionyl]-4-(phenylthio)-L-proline calcium salt or hemi-calcium salt. The present invention further relates to a process for the preparation of the new crystalline form of zofenopril calcium, its use in pharmaceutical compositions and the use of the new crystalline form and compositions in the treatment of hypertension and various other diseases.

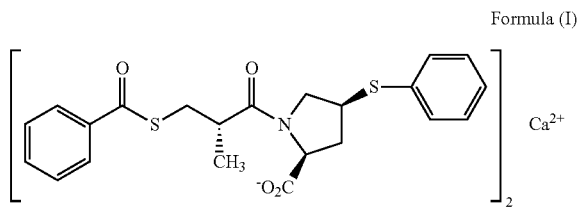

Formula (I)

BACKGROUND OF THE INVENTION

Zofenopril is a non-peptidic orally active sulphydryl ACE inhibitor with long lasting action for the treatment of hypertension. It is currently approved in the form of the calcium salt for the treatment of hypertension.

Prior art forms of zofenopril calcium comprise a monohydrate form designated form C disclosed in international patent application WO 2007/003963 and two anhydrous forms both disclosed in U.S. Pat. Nos. 6,515,012 and 6,521,760 and designated forms A and B.

One requirement of a pharmaceutically acceptable active ingredient is that it should have an advantageous dissolution profile which is an important contributory factor in the bioavailability of a pharmaceutical compound. There are many avenues open to the skilled person in order to enhance the dissolution profile of an active pharmaceutical ingredient (API) and subsequently a pharmaceutical composition containing the API. These include reducing the particle size of the API, adding a surfactant to the composition or utilising different forms of the compound such as salts, solvates or crystalline forms having an advantageous dissolution profile. This latter route forms the basis of the present application. It is generally expected by those skilled in the art that hydrated forms of a chemical compound usually exhibit decreased solubility levels in aqueous media compared to anhydrous forms. Thus, it is advantageous to provide stable anhydrous forms of a pharmaceutical compound.

U.S. Pat. Nos. 6,515,012 and 6,521,760 discuss the prior art disclosed in U.S. Pat. No. 4,316,906 and describe the method for the preparation of zofenopril calcium as disclosed in U.S. Pat. No. 4,316,906 as comprising the following steps:

(a) condensation between cis-4-(phenylthio)-L-proline and D-3-(benzoylthio)-2-methylpropionyl chloride in aqueous solution keeping the pH at values of 8-8.5 by addition of 5N sodium hydroxide, subsequent acidification with HCl, extraction with isobutyl acetate and concentration of the extracts, washing with saline solution, to give (4S)-1-[(2S)-3-(benzoylthio)-2-methylpropinoyl]-4-(phenylthio)-L-proline;

(b) treatment of the resinous material from the previous step in isopropanol solution with potassium 2-ethyl-hexanoate to obtain the corresponding potassium salt;

(c) dissolution of the potassium salt in water to a 5% concentration and very slow addition, with simultaneous seeding, of a slight excess of a 2N calcium chloride aqueous solution to precipitate the desired calcium salt, washing the resulting product thoroughly with water, drying under vacuum at a comparatively high temperature to give the desired calcium salt as dry powder with a melting point of about 250° C.;

(d) alternatively (4S)-1-[(2S)-3-(benzoylthio)-2-methylpropinoyl]-4-(phenylthio)-L-proline is dissolved in ethanol and treated with the same volume of an aqueous suspension containing one equivalent of calcium oxide; after removing ethanol and subsequently washing with ether, the aqueous suspension is freeze-dried to obtain the calcium salt with a melting point of 235-237° C.

According to U.S. Pat. Nos. 6,515,012 and 6,521,760, the synthesis described in U.S. Pat. No. 4,316,906 (cited above at points a, b and c) mainly yields polymorph A, but also polymorph B in very variable percentages and never below 20%. Moreover, the alternative synthesis described (cited at point d) affords a partially amorphous product with very variable characteristics, in which polymorph A, when present, is in concentrations much lower than those obtained in the preceding process.

U.S. Pat. Nos. 6,515,012 and 6,521,760 both disclose a process for the preparation of substantially pure polymorph A of zofenopril calcium comprising the following steps:

(a) reaction of (S)(–)-3-(benzoylthio)-2-methyl-propanoic acid chloride and cis-4-(phenylthio)-L-proline in water at a pH ranging from 9.0-9.5 and recovery of zofenopril in the acidic form, (b) salification of acid zofenopril with a potassium salt in alcoholic solution and recovery of the resulting potassium salt, (c) conversion of the potassium salt to calcium by addition of an aqueous solution of zofenopril potassium salt to a calcium chloride aqueous solution at 70-90° C. with simultaneous seeding to promote the precipitation of polymorph A.

The synthesis disclosed in the aforementioned US patents for the preparation of polymorph A has the following drawbacks:

The reaction is carried out at a relatively high temperature (80-85° C.) at which inter-conversion of the polymorphs is possible.

Substantially pure polymorph A can be obtained from the above process, but the possibility of traces of polymorph B cannot be ruled out.

The aforementioned US patents also disclose a process for the preparation of polymorph B comprising the following steps:

(a) A solution of zofenopril potassium salt (0.27M) is sprayed in lukewarm water (55° C.), while adding a calcium chloride solution, the solution being such that the total amounts of drug and calcium chloride are equimolar.
(b) The resulting suspension containing the slurry product is heated at 85° C. for 12-14 hours to obtain complete conversion to polymorph B.
(c) After cooling at about 25° C., the product is filtered, washed with water until it is substantially free from chloride ions, and then dried under vacuum.

The present inventors have found the following potential and actual disadvantages with the prior art forms A and B:

The absorption of considerable amounts of moisture can lead to the reversion to a hydrated form.

The absorption of moisture can result in 'sticky' compounds that are a problem during formulation of the compound into pharmaceutical combinations.

The absorption of considerable amounts of water can have an impact on the dissolution profile and cause an inconsistent dissolution profile.

The absorption of moisture can induce degradation processes not only of the API, but also of potentially susceptible excipients that may be used in the drug product.

Thus, it would be advantageous to provide novel anhydrous crystalline forms of zofenopril calcium that are essentially non-hygroscopic and can overcome the problems associated with the prior art forms. It would also be advantageous to provide a compound that shows increased dissolution kinetics and is hygroscopically stable.

SUMMARY OF THE INVENTION

Accordingly, in a first aspect of the invention there is provided zofenopril calcium crystalline form D comprising characteristic XRPD peaks at two or more (preferably three or more, four or more, five or more, six or more, seven or more, eight or more, or nine) of 17.7, 18.0, 18.3, 19.2, 19.5, 19.9, 20.5, 21.9 and 23.1±0.2 °2θ.

The first aspect of the present invention also provides zofenopril calcium crystalline form D comprising substantially the characteristic XRPD peaks shown in Table 1:

TABLE 1 showing characteristic XRPD peaks of zofenopril calcium crystalline form D according to the invention

| Angle 2-Theta | d value (Angstrom) |
|---|---|
| 4.2 | 20.84 |
| 4.8 | 18.43 |
| 7.7 | 11.48 |
| 8.9 | 9.91 |
| 9.6 | 9.17 |
| 11.5 | 7.68 |
| 13.5 | 6.53 |
| 13.7 | 6.44 |
| 15.5 | 5.70 |
| 17.1 | 5.18 |
| 17.7 | 5.02 |
| 18.0 | 4.93 |
| 18.3 | 4.83 |
| 19.2 | 4.61 |
| 19.5 | 4.55 |
| 19.9 | 4.45 |
| 20.5 | 4.32 |
| 20.9 | 4.25 |
| 21.3 | 4.17 |
| 21.9 | 4.06 |
| 22.4 | 3.97 |
| 23.1 | 3.85 |
| 24.2 | 3.68 |
| 24.5 | 3.63 |

TABLE 1-continued showing characteristic XRPD peaks of zofenopril calcium crystalline form D according to the invention

| Angle 2-Theta | d value (Angstrom) |
|---|---|
| 25.2 | 3.53 |
| 25.8 | 3.45 |
| 26.1 | 3.41 |
| 26.7 | 3.34 |
| 27.3 | 3.27 |
| 27.8 | 3.21 |

The first aspect of the present invention also provides zofenopril calcium crystalline form D having an XRPD pattern substantially as shown in FIG. 1.

Figure 2:
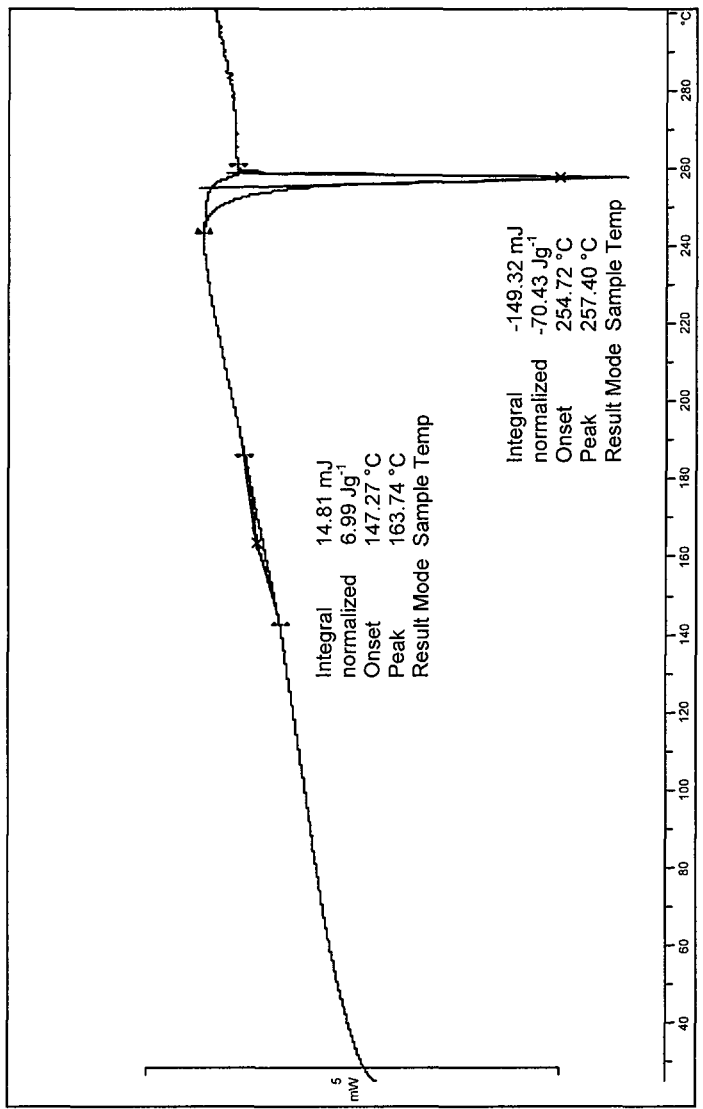

The first aspect of the present invention also provides zofenopril calcium crystalline form D having a DSC heating trace substantially as shown in FIG. 2. Preferably the zofenopril calcium crystalline form D is characterized by a DSC with an endothermic peak at about 257° C.

Figure 3:
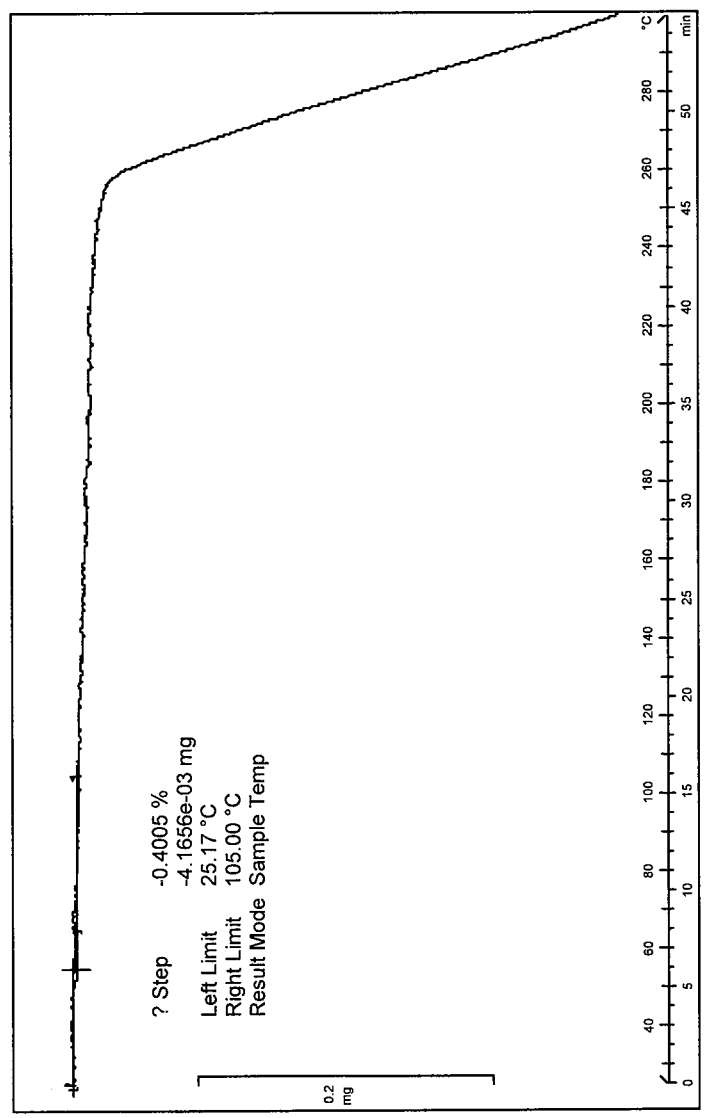

The first aspect of the present invention also provides zofenopril calcium crystalline form D having a TGA heating trace substantially as shown in FIG. 3.

Figure 4:
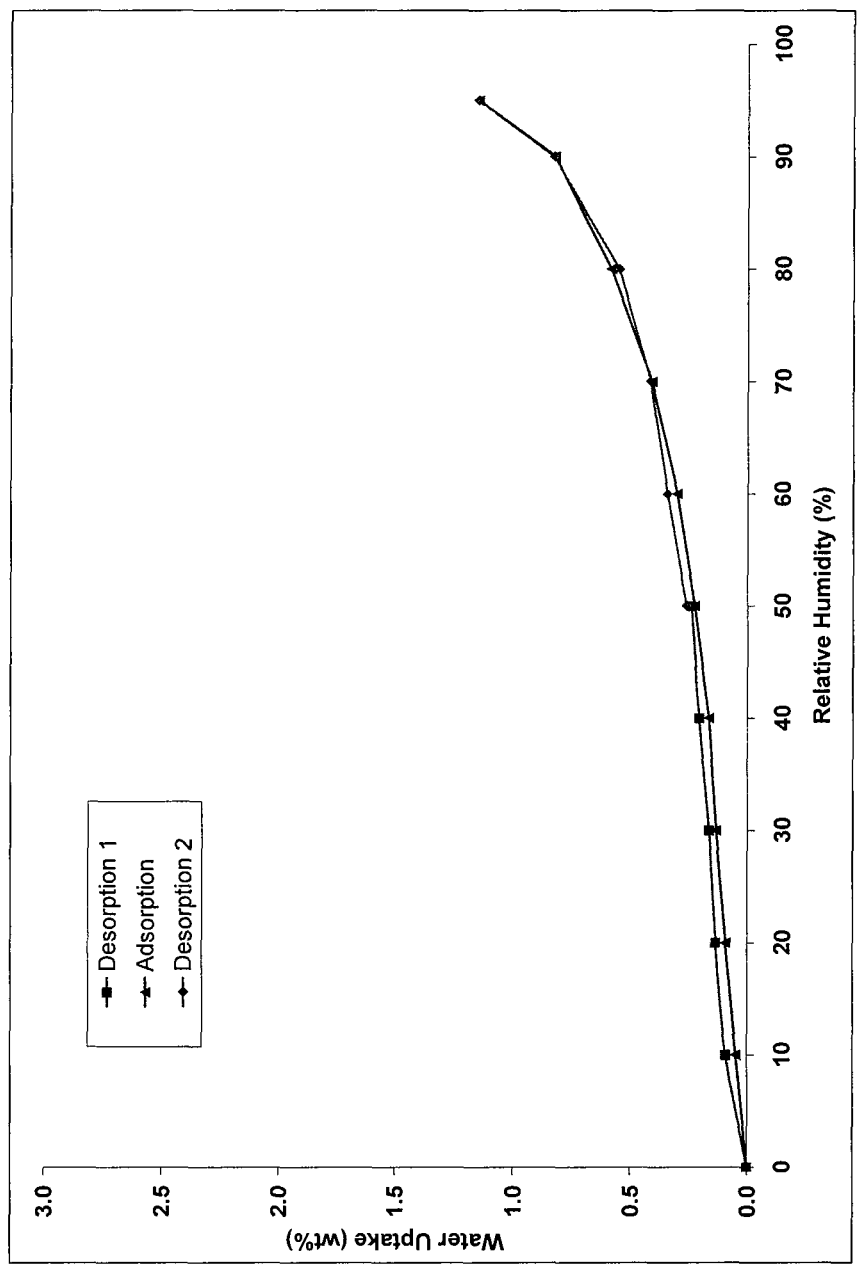

The first aspect of the present invention also provides zofenopril calcium crystalline form D having a water vapour sorption isotherm substantially as shown in FIG. 4.

Preferably the zofenopril calcium crystalline form D is characterized by a water vapour sorption isotherm showing a water uptake of less than 0.5 wt % up to a relative humidity level of 70% rh and/or a water uptake of less than 1 wt % up to a relative humidity level of 90% rh.

In certain preferred embodiments of the first aspect of the invention, zofenopril calcium crystalline form D is provided wherein the zofenopril calcium comprises less than 10% of zofenopril calcium in other polymorphic or amorphous forms, preferably the zofenopril calcium comprises less than 5% of zofenopril calcium in other polymorphic or amorphous forms, more preferably the zofenopril calcium comprises less than 1% of zofenopril calcium in other polymorphic or amorphous forms, and most preferably the zofenopril calcium comprises less than 0.1% of zofenopril calcium in other polymorphic or amorphous forms. Thus, preferably the zofenopril calcium crystalline form D of the present invention has a polymorphic purity of at least 90%, preferably at least 95%, preferably at least 99%, preferably at least 99.9%, as measured by XRPD or DSC.

In further embodiments of the first aspect according to the invention, the zofenopril calcium crystalline form D comprises less than 5% of chemical impurities other than zofenopril calcium in other polymorphic or amorphous forms, preferably less than 3%, preferably less than 2%, preferably less than 1%. Thus, preferably the zofenopril calcium crystalline form D of the present invention has a chemical purity of at least 95%, preferably at least 97%, preferably at least 98%, preferably at least 99%, as measured by HPLC.

The zofenopril calcium crystalline form D of the first aspect of the present invention is suitable for use as a medicament, preferably for use as an ACE inhibitor, more preferably for use in reducing blood pressure or in an alternative embodiment for treating or preventing hypertension, cardiac decompensation, myocardial infarction, acute myocardial infarction, heart failure or chronic heart failure.

It has been found by the inventors that zofenopril calcium crystalline form D according to the invention has a number of surprising qualities and advantages over the prior art forms. The non-hygroscopic behaviour of the novel anhydrous form results in a product with a controlled and low water content throughout the entire relative humidity range, which is beneficial in terms of a number of properties:

- less potential for occurrence of hydrolysis and other water-induced breakdown processes.
- less potential for induction of fractional conversion from the calcium salt to the free acid due to the presence of water. The free acid usually has decreased solubility levels compared to a carboxylate salt form.
- less potential for stickiness of API particles as a consequence of inter-particle bridging by water.
- being anhydrous, form D shows more advantageous dissolution kinetics, since anhydrous forms generally exhibit better solubility levels in aqueous media compared to hydrated forms.

Further, although not wishing to be bound by theory, form D is expected to exhibit increased rates of dissolution compared to prior art form B, since a smaller lattice enthalpy has to be overcome during the dissolution process of form D.

Thermogravimetric analysis (TGA) on novel anhydrous form D revealed that no significant weight loss is encountered up to temperatures of approximately 260° C. (see FIG. 3), where degradation processes start. The weight loss detected from 25-105° C., which is equivalent to the loss on drying (LOD), is less than 0.5 wt %, which confirms that novel anhydrous form D contains no significant amounts of residual solvents, including water.

Figure 5:
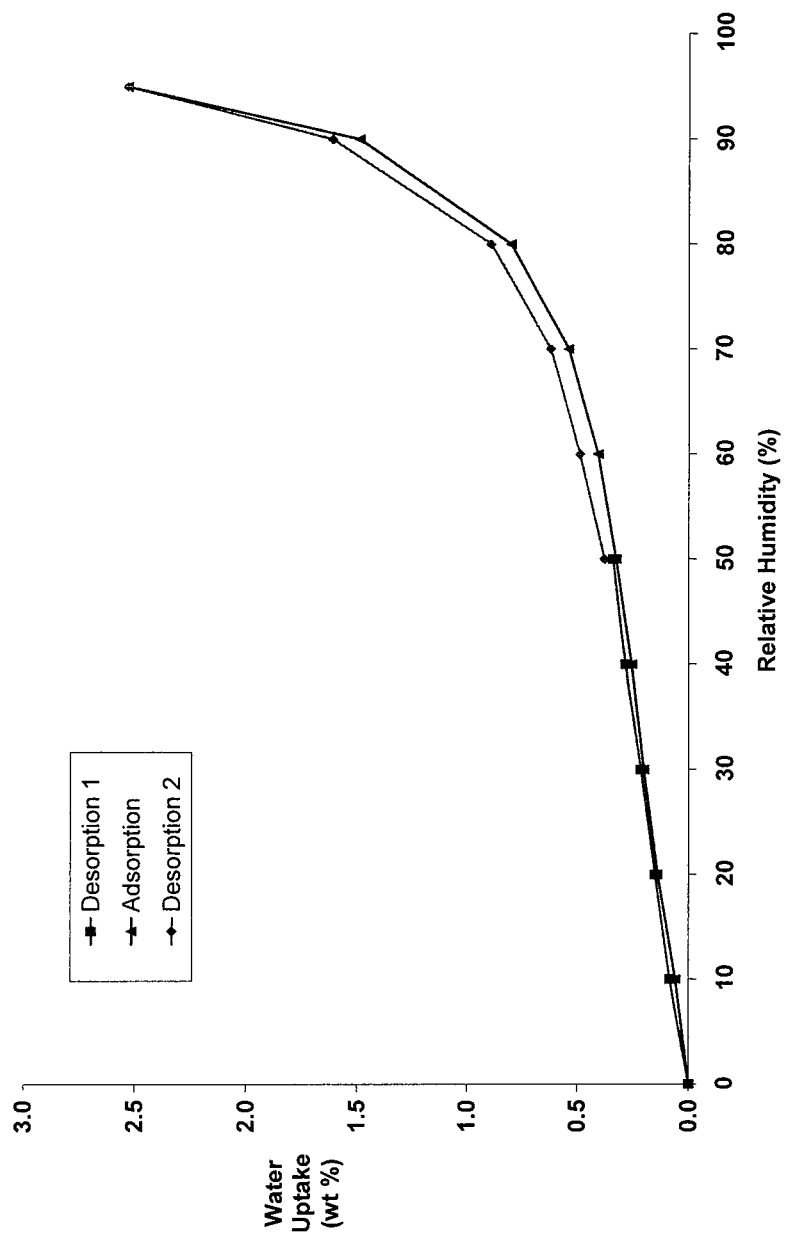

Moreover, water vapour sorption studies on novel anhydrous form D, the results of which are shown in FIG. 4, showed that this form absorbs only small amounts of water throughout the entire relative humidity range of 0-95% rh. Equilibrium water uptake levels of less than 0.5 wt % were observed up to a relative humidity level of 70% rh, which may be considered the uppermost limit of ambient humidity conditions. Exposure to high relative humidity levels of greater than 90% rh showed a maximum water uptake of ca. 1 wt %, which still can be considered a low water content. Comparison with equivalent studies on prior art form B showed that form B exhibits a significantly increased maximum water uptake level of approximately 2.5 wt % at elevated relative humidity levels. The results of these water vapour sorption studies on the prior art form B are shown in FIG. 5.

In addition, the water vapour sorption isotherm showed that anhydrous form D does not easily re-convert to hydrate form C upon being exposed to water vapour. This again confirms that novel anhydrous form D can be considered as being sufficiently stable at room temperature.

Thus, zofenopril calcium crystalline form D of the first aspect of the present invention is an anhydrous crystalline form, it is essentially non-hygroscopic, it is substantially hygroscopically stable, and it is expected to have an advantageous dissolution profile compared to the prior art forms of zofenopril calcium.

A second aspect provides a process for preparing zofenopril calcium crystalline form D according to the first aspect, comprising drying a hydrated form of zofenopril calcium, preferably under an inert atmosphere. In a particularly preferred embodiment, the inert atmosphere is a nitrogen flow atmosphere, which in further preferred embodiments has a flow rate of about 500 ml/min.

In other embodiments, the process comprises drying the hydrated zofenopril calcium preferably at between 40° C.-140° C. Preferably the hydrated zofenopril calcium is dried until the moisture content falls below about 1%, more preferably until the moisture content falls below about 0.5%. The time taken for the hydrated zofenopril calcium to dry is also an important embodiment. Accordingly, in a preferred embodiment the hydrated zofenopril calcium is dried for approximately 120 minutes or less, more preferably for approximately 60 minutes or less, most preferably for approximately 30 minutes or less. In further preferred embodiments, the hydrated zofenopril calcium is hydrated form C.

In a third aspect according to the invention, a pharmaceutical composition is provided, comprising zofenopril calcium crystalline form D according to any of the previously described aspects of the invention. In preferred embodiments the composition further comprises one or more pharmaceutically acceptable carrier(s), excipient(s) or diluent(s).

A particularly preferred embodiment provides that the composition is for oral or parenteral administration. For example, preferred embodiments comprise compositions in the form of a tablet, capsule, syrup, suspension or elixir for oral administration or in a form suitable for preparing a syrup, suspension or elixir for oral administration. Other preferred embodiments comprise compositions in the form of a sterile solution or suspension for parenteral administration or in a form suitable for preparing a sterile solution or suspension for parenteral administration. In further preferred embodiments, the composition is in unit dosage form comprising zofenopril calcium according to the invention in an amount of from 1 mg to 500 mg.

In another embodiment, a pharmaceutical composition is provided for use as an ACE inhibitor, preferably for reducing blood pressure or in alternative embodiments for treating or preventing hypertension, cardiac decompensation, myocardial infarction, acute myocardial infarction, heart failure or chronic heart failure.

A fourth aspect according to the invention provides a method of reducing blood pressure, comprising administering a therapeutically effective amount of zofenopril calcium crystalline form D according to any aspect or embodiment hereinbefore mentioned to a patient in need thereof.

A fifth aspect provides a method of treating or preventing hypertension, cardiac decompensation, myocardial infarction, acute myocardial infarction, heart failure or chronic heart failure, comprising administering a therapeutically effective amount of zofenopril calcium crystalline form D according to any aspect or embodiment hereinbefore mentioned to a patient in need thereof.

In preferred embodiments of the fourth and fifth aspects according to the invention, the patient is a mammal, preferably a human.

In further preferred embodiments of the fourth and fifth aspects, the amount of zofenopril calcium crystalline form D administered is from 0.1 mg to 100 mg per kg per day.

A sixth aspect according to the invention provides the use of zofenopril calcium crystalline form D according to any aspect hereinbefore mentioned for the manufacture of a medicament for reducing blood pressure.

A seventh aspect provides the use of zofenopril calcium crystalline form D according to any aspect hereinbefore mentioned for the manufacture of a medicament for treating or preventing hypertension, cardiac decompensation, myocardial infarction, acute myocardial infarction, heart failure or chronic heart failure.

BRIEF DESCRIPTION OF THE ACCOMPANYING FIGURES

FIG. 1: X-Ray Powder Diffraction (XRPD) pattern of zofenopril calcium crystalline form D according to the invention.

FIG. 2: Differential Scanning calorimetry (DSC) heating trace of zofenopril calcium crystalline form D according to the invention.

FIG. 3: Thermogravimetric Analysis (TGA) heating trace of zofenopril calcium crystalline form D according to the invention.

FIG. 4: Water Vapour Sorption Isotherm of zofenopril calcium crystalline form D according to the invention.

FIG. 5: Water Vapour Sorption Isotherm of zofenopril calcium prior art form B.

Figure 6:
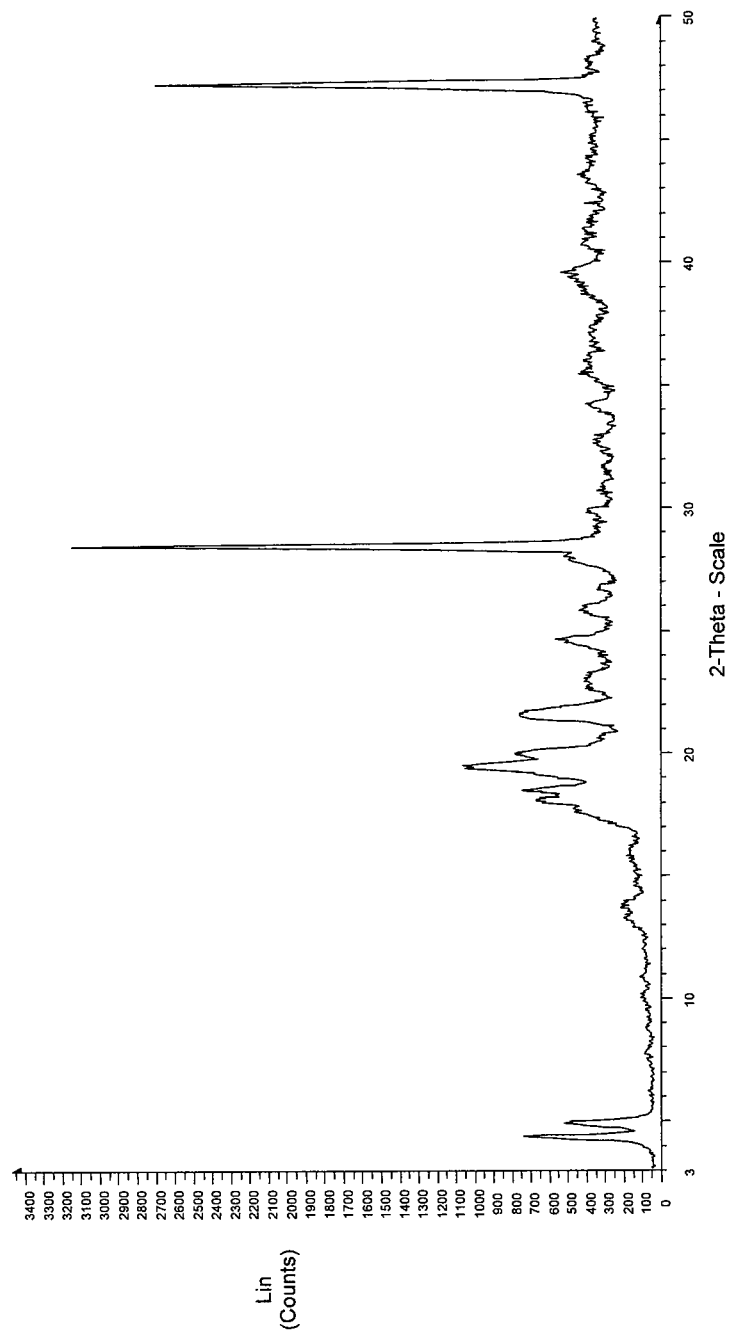

FIG. 6 X-Ray Powder Diffraction (XRPD) pattern of zofenopril calcium prior art form B.

DETAILED DESCRIPTION OF THE INVENTION

The terms 'crystalline form' and 'polymorphic form' are used interchangeably herein.

The X-ray powder diffraction data was obtained by methods known in the art using a Bruker D8 Advance Powder Diffractometer with scintillation detector under the following parameters:
Reflectance mode
Cu Kα radiation (1.5406 Å)
Scanning range: 2-30 °2θ
Step size: 0.02 °2θ
Time per step: 6s The resultant XRPD traces are shown in FIG. 1 which represents the zofenopril calcium crystalline form D according to the invention and in FIG. 6 which shows the prior art form B.

The compounds obtained by the processes according to the invention as described above and in the following examples were also subjected to differential scanning calorimetry (DSC). The resulting trace is shown in FIG. 2. The DSC thermal analysis data was obtained using a Mettler-Toledo DSC821e apparatus under the following parameters:
Temperature profile: 25-300° C.@5° C./min
Nitrogen purge gas: 50 ml/min
Aluminium pan: 40 µl, pierced prior to scan The compounds obtained by the processes according to the invention as described above and in the following examples were also subjected to thermogravimetric analysis (TGA). An exemplary TGA trace is shown in FIG. 3. It can be seen that the form D according to the invention is chemically stable at processing temperatures and storage temperatures, i.e. degradation by conversion to other polymorphic forms is not seen. Indeed, DSC and XRPD experiments indicate that no polymorphic transition of crystalline form D occurs up to temperatures of ca. 140° C. The TGA analysis data was obtained using a Mettler-Toledo TGA851e apparatus under the following parameters:
Temperature profile: 25-300° C.@5° C./min
Nitrogen purge gas: 50 ml/min
Aluminium pan: 40 µl, pierced prior to scan Determination of the water vapour sorption isotherms of zofenopril calcium crystalline form D according to the invention and of the prior art form B were performed by Surface Measurement Systems DVS-HT. The resultant isotherms, as shown in FIGS. 4 and 5 respectively, were obtained under the following parameters:
Temperature=25° C.
Humidity profile: Desorption 1: 50-0% relative humidity (rh) in steps of 10%
Adsorption: 0-90% rh in steps of 10%, 95% rh
Desorption 2: 95% rh, 90-50% rh in steps of 10%
Equilibration time per rh stage: 240 min (0% rh), 180 min (all other rh levels)

Illustrative of the invention is a pharmaceutical composition made by mixing crystalline form D zofenopril calcium according to the invention and a pharmaceutically acceptable carrier. An example of the invention is a method for the treatment or prevention of an angiotensin type II receptor mediated disorder in a subject in need thereof, comprising administering to the subject a therapeutically or prophylactically effective amount of zofenopril calcium crystalline form D according to any of the embodiments of the invention or of the pharmaceutical composition described above. Also included in the invention is the use of zofenopril calcium crystalline form D, which in preferred embodiments is substantially free of other forms of zofenopril calcium, for the preparation of a medicament for use as an ACE inhibitor.

Pharmaceutical compositions of the present invention contain zofenopril calcium crystalline form D. It is preferred that the zofenopril calcium crystalline form D is substantially pure, but this is non-limiting to the working of the invention. The zofenopril calcium crystalline form D, prepared by the processes of the present invention or indeed by any other process envisaged by the skilled person, is ideal for formulation of pharmaceutical products. In addition to the active ingredient(s), the pharmaceutical compositions of the present invention may contain one or more excipients.

Excipients are added to the composition for a variety of purposes. Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulphate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. Carbopol®), carboxymethyl cellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminium silicate, maltodextrin, methyl cellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethyl cellulose calcium, carboxymethyl cellulose sodium (e.g. Ac-Di-Sol®, Primellose®), colloidal silicon dioxide, croscarmellose sodium, crospovidone (e.g. Kollidon®, Polyplasdone®), guar gum, magnesium aluminium silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulphate, sodium stearyl fumarate, stearic acid, talc and zinc stearate.

Flavouring agents and flavour enhancers make the dosage form more palatable to the patient. Common flavouring agents and flavour enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colourant to improve their appearance and/or facilitate patient identification of the product and unit dosage level.

In the process of preparing liquid pharmaceutical compositions of the present invention, the zofenopril calcium according to the invention and any other solid excipients are dissolved, partially dissolved or suspended in a liquid carrier such as water, vegetable oil, alcohol, polyethylene glycol, propylene glycol or glycerin.

Thus, in a further aspect of the present invention, there is provided a process for preparing a liquid pharmaceutical composition comprising zofenopril calcium, wherein the process comprises dissolving, partially dissolving, or suspending zofenopril calcium crystalline form D according to the invention in a liquid carrier such as water, vegetable oil, alcohol, polyethylene glycol, propylene glycol or glycerin.

Liquid pharmaceutical compositions may further contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel or organoleptic qualities of the product and/or coat the lining of the gastrointestinal tract. Such agents include acacia, alginic acid, bentonite, carbomer, carboxymethyl cellulose calcium or sodium, cetostearyl alcohol, methyl cellulose, ethyl cellulose, gelatin, guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxytoluene, butylated hydroxyanisole and ethylenediaminetetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well known in the pharmaceutical arts. Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or a soft shell. The shell may be made from gelatin and optionally contain a plasticizer such as glycerin and sorbitol, and an opacifying agent or colourant. The active ingredient and excipients may be formulated into compositions and dosage forms according to methods known in the art.

A composition for tableting or capsule filling may be prepared by wet granulation. In wet granulation, some or all of the active ingredient and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The following paragraphs enumerated consecutively from 1 through 42 provide for various aspects of the present invention. In one embodiment, the present invention provides:
1. Zofenopril calcium crystalline form D comprising characteristic XRPD peaks at two or more of 17.7, 18.0, 18.3, 19.2, 19.5, 19.9, 20.5, 21.9 and 23.1±0.2 °2θ.
2. Zofenopril calcium crystalline form D comprising substantially the following characteristic XRPD peaks:

| Angle 2-Theta | d value (Angstrom) |
|---|---|
| 4.2 | 20.84 |
| 4.8 | 18.43 |
| 7.7 | 11.48 |
| 8.9 | 9.91 |
| 9.6 | 9.17 |
| 11.5 | 7.68 |
| 13.5 | 6.53 |
| 13.7 | 6.44 |
| 15.5 | 5.70 |
| 17.1 | 5.18 |
| 17.7 | 5.02 |
| 18.0 | 4.93 |
| 18.3 | 4.83 |
| 19.2 | 4.61 |
| 19.5 | 4.55 |
| 19.9 | 4.45 |
| 20.5 | 4.32 |
| 20.9 | 4.25 |
| 21.3 | 4.17 |
| 21.9 | 4.06 |
| 22.4 | 3.97 |
| 23.1 | 3.85 |
| 24.2 | 3.68 |
| 24.5 | 3.63 |
| 25.2 | 3.53 |
| 25.8 | 3.45 |
| 26.1 | 3.41 |
| 26.7 | 3.34 |
| 27.3 | 3.27 |
| 27.8 | 3.21 |

3. Zofenopril calcium crystalline form D having an XRPD pattern substantially as shown in FIG. 1.

4. Zofenopril calcium crystalline form D having a DSC heating trace substantially as shown in FIG. 2.

5. Zofenopril calcium crystalline form D having a TGA heating trace substantially as shown in FIG. 3.

6. Zofenopril calcium crystalline form D having a water vapour sorption isotherm substantially as shown in FIG. 4.

7. Zofenopril calcium crystalline form D according to any one of the preceding paragraphs, wherein the zofenopril calcium comprises less than 10% of zofenopril calcium in other polymorphic or amorphous forms.

8. Zofenopril calcium crystalline form D according to paragraph 7, wherein the zofenopril calcium comprises less than 5% of zofenopril calcium in other polymorphic or amorphous forms.

9. Zofenopril calcium crystalline form D according to paragraph 8, wherein the zofenopril calcium comprises less than 1% of zofenopril calcium in other polymorphic or amorphous forms.

10. Zofenopril calcium crystalline form D according to paragraph 9, wherein the zofenopril calcium comprises less than 0.1% of zofenopril calcium in other polymorphic or amorphous forms.

11. Zofenopril calcium crystalline form D according to any one of the preceding paragraphs, wherein the zofenopril calcium comprises less than 3% of chemical impurities other than zofenopril calcium in other polymorphic or amorphous forms.

12. Zofenopril calcium crystalline form D according to any one of the preceding paragraphs, for use as a medicament.

13. Zofenopril calcium crystalline form D according to any one of the preceding paragraphs, for use as an ACE inhibitor.

14. Zofenopril calcium crystalline form D according to any one of the preceding paragraphs, for reducing blood pressure.

15. Zofenopril calcium crystalline form D according to any one of the preceding paragraphs, for treating or preventing hypertension, cardiac decompensation, myocardial infarction, acute myocardial infarction, heart failure or chronic heart failure.

16. A process for preparing zofenopril calcium crystalline form D according to any one of paragraphs 1 to 15, comprising drying a hydrated form of zofenopril calcium.

17. A process according to paragraph 16, wherein the hydrated zofenopril calcium is dried under an inert atmosphere.

18. A process according to paragraph 17, wherein the inert atmosphere is a nitrogen flow atmosphere.

19. A process according to paragraph 18, wherein the flow rate of the nitrogen flow atmosphere is about 500 ml/min.

20. A process according to any one of paragraphs 16 to 19, wherein the hydrated zofenopril calcium is hydrated form C.

21. A process according to any one of paragraphs 16 to 20, wherein the hydrated zofenopril calcium is dried at between 40° C.-140° C.

22. A process according to any one of paragraphs 16 to 21, wherein the hydrated zofenopril calcium is dried until the moisture content is less than about 1%.

23. A process according to paragraph 22, wherein the hydrated zofenopril calcium is dried until the moisture content is less than about 0.5%.

24. A process according to any one of paragraphs 16 to 23, wherein the hydrated zofenopril calcium is dried for approximately 120 minutes or less.

25. A process according to paragraph 24, wherein the hydrated zofenopril calcium is dried for approximately 60 minutes or less.

26. A process according to paragraph 25, wherein the hydrated zofenopril calcium is dried for approximately 30 minutes or less.

27. A pharmaceutical composition comprising zofenopril calcium crystalline form D according to any one of paragraphs 1 to 15 or prepared by a process according to any one of paragraphs 16 to 26.

28. A pharmaceutical composition according to paragraph 27, further comprising one or more pharmaceutically acceptable carrier(s), excipient(s) or diluent(s).

29. A pharmaceutical composition according to paragraph 27 or 28, wherein the composition is for oral or parenteral administration.

30. A pharmaceutical composition according to any one of paragraphs 27 to 29, wherein the composition is in the form of a tablet, capsule, syrup, suspension or elixir for oral administration or in a form suitable for preparing a syrup, suspension or elixir for oral administration.

31. A pharmaceutical composition according to any one of paragraphs 27 to 29, wherein the composition is in the form of a sterile solution or suspension for parenteral administration or in a form suitable for preparing a sterile solution or suspension for parenteral administration.

32. A pharmaceutical composition according to any one of paragraphs 27 to 31, wherein the composition is in unit dosage form comprising zofenopril calcium crystalline form D in an amount of from 1 mg to 500 mg.

33. A pharmaceutical composition according to any one of paragraphs 27 to 32, for use as an ACE inhibitor.

34. A pharmaceutical composition according to any one of paragraphs 27 to 33, for reducing blood pressure.

35. A pharmaceutical composition according to any one of paragraphs 27 to 34, for treating or preventing hypertension, cardiac decompensation, myocardial infarction, acute myocardial infarction, heart failure or chronic heart failure.

36. A method of reducing blood pressure, comprising administering a therapeutically effective amount of zofenopril calcium crystalline form D according to any one of paragraphs 1 to 15 or prepared by a process according to any one of paragraphs 16 to 26, or administering a therapeutically effective amount of a composition according to any one of paragraphs 27 to 35, to a patient in need thereof 37. A method of treating or preventing hypertension, cardiac decompensation, myocardial infarction, acute myocardial infarction, heart failure or chronic heart failure, comprising administering a therapeutically or prophylactically effective amount of zofenopril calcium crystalline form D according to any one of paragraphs 1 to 15 or prepared by a process according to any one of paragraphs 16 to 26, or administering a therapeutically or prophylactically effective amount of a composition according to any one of paragraphs 27 to 35, to a patient in need thereof 38. A method according to paragraph 36 or 37, wherein the patient is a mammal.

39. A method according to paragraph 38, wherein the patient is a human.

40. A method according to any one of paragraphs 36 to 39, wherein the amount of zofenopril calcium crystalline form D administered is from 0.1 mg to 100 mg per kg per day.

41. Use of zofenopril calcium crystalline form D according to any one of paragraphs 1 to 15 or prepared by a process according to any one of paragraphs 16 to 26, for the manufacture of a medicament for reducing blood pressure.

42. Use of zofenopril calcium crystalline form D according to any one of paragraphs 1 to 15 or prepared by a process according to any one of paragraphs 16 to 26, for the manufacture of a medicament for treating or preventing hypertension, cardiac decompensation, myocardial infarction, acute myocardial infarction, heart failure or chronic heart failure.

Certain aspects of the invention are illustrated in more detail by the following non-limiting examples.

EXAMPLES

The following examples show processes according to the invention to prepare the novel anhydrous form D of zofenopril calcium according to the invention. They comprise the drying of zofenopril calcium hydrate form C at elevated temperatures in a dry nitrogen atmosphere.

Example 1

Approximately 100 mg of zofenopril calcium were dried at 50° C. for 120 minutes under a nitrogen flow atmosphere (flow rate: 500 ml/min). The sample was finally conditioned at 30° C. for 30 minutes under the nitrogen gas atmosphere.

Example 2

Approximately 100 mg of zofenopril calcium were dried at 50° C. for 30 minutes under a nitrogen flow atmosphere (flow rate: 500 ml/min). The sample was finally conditioned at 30° C. for 30 minutes under the nitrogen gas atmosphere.

Example 3

Approximately 100 mg of zofenopril calcium were dried at 70° C. for 30 minutes under a nitrogen flow atmosphere (flow rate: 500 ml/min). The sample was finally conditioned at 30° C. for 30 minutes under the nitrogen gas atmosphere.

Example 4

Approximately 100 mg of zofenopril calcium were dried at 90° C. for 30 minutes under a nitrogen flow atmosphere (flow rate: 500 ml/min). The sample was finally conditioned at 30° C. for 30 minutes under the nitrogen gas atmosphere.

Example 5

Approximately 100 mg of zofenopril calcium were dried at 110° C. for 30 minutes under a nitrogen flow atmosphere (flow rate: 500 ml/min). The sample was finally conditioned at 30° C. for 30 minutes under the nitrogen gas atmosphere.

The drying processes as detailed in the above examples yield the novel anhydrous form D of zofenopril calcium according to the invention. All the resultant crystalline compounds of the above examples were characterised by X-ray powder diffraction (XRPD) and all comprised reflexes as compiled in Table 1 and an XRPD diffraction pattern as displayed in FIG. 1. Thus, the compounds prepared by examples 1-5 were determined to be the same crystalline form and were distinct from the prior art forms A, B, and C. Further, the samples were then 'conditioned', i.e. they were allowed to equilibrate. This showed that there was no conversion of the resultant form D upon cooling, either back to the hydrated form C or to another less advantageous crystalline form, and is again an indication that form D according to the invention is stable and has utility in pharmaceutical compositions.

What is claimed is:

1. A zofenopril calcium crystalline form:
   (i) comprising characteristic XRPD peaks at seven or more of 17.7, 18.0, 18.3, 19.2, 19.5, 19.9, 20.5, 21.9 and 23.1±0.2° 2θ; and
   (ii) having a DSC heating trace substantially as shown in FIG. 2; and/or
   (iii) having a TGA heating trace substantially as shown in FIG. 3; and/or
   (iv) having a water vapour sorption isotherm substantially as shown in FIG. 4.

2. The zofenopril calcium crystalline form according to claim 1, comprising substantially the following characteristic XRPD peaks:

| Angle 2-Theta | d value (Angstrom) |
|---|---|
| 4.2 | 20.84 |
| 4.8 | 18.43 |
| 7.7 | 11.48 |
| 8.9 | 9.91 |
| 9.6 | 9.17 |
| 11.5 | 7.68 |
| 13.5 | 6.53 |
| 13.7 | 6.44 |
| 15.5 | 5.70 |
| 17.1 | 5.18 |
| 17.7 | 5.02 |
| 18.0 | 4.93 |
| 18.3 | 4.83 |
| 19.2 | 4.61 |
| 19.5 | 4.55 |
| 19.9 | 4.45 |
| 20.5 | 4.32 |
| 20.9 | 4.25 |
| 21.3 | 4.17 |
| 21.9 | 4.06 |

-continued

| Angle 2-Theta | d value (Angstrom) |
|---|---|
| 22.4 | 3.97 |
| 23.1 | 3.85 |
| 24.2 | 3.68 |
| 24.5 | 3.63 |
| 25.2 | 3.53 |
| 25.8 | 3.45 |
| 26.1 | 3.41 |
| 26.7 | 3.34 |
| 27.3 | 3.27 |
| 27.8 | 3.21. |

3. The zofenopril calcium crystalline form according to claim 1, having an XRPD pattern substantially as shown in FIG. 1.

4. The zofenopril calcium crystalline form according to claim 1, wherein:
   (i) the zofenopril calcium comprises less than 10% of zofenopril calcium in other polymorphic or amorphous forms; or
   (ii) the zofenopril calcium comprises less than 5% of zofenopril calcium in other polymorphic or amorphous forms; or
   (iii) the zofenopril calcium comprises less than 1% of zofenopril calcium in other polymorphic or amorphous forms; or
   (iv) the zofenopril calcium comprises less than 0.1% of zofenopril calcium in other polymorphic or amorphous forms.

5. A process for preparing the zofenopril calcium crystalline form according to claim 1, comprising drying a hydrated form of zofenopril calcium under an inert nitrogen flow atmosphere.

6. A pharmaceutical composition comprising the zofenopril calcium crystalline form according to claim 1.

7. A pharmaceutical composition according to claim 6:
   (i) further comprising one or more pharmaceutically acceptable carrier(s), excipient(s) or diluent(s); and/or
   (ii) wherein the composition is for oral or parenteral administration; and/or
   (iii) wherein the composition is in the form of a tablet, capsule, syrup, suspension or elixir for oral administration or in a form suitable for preparing a syrup, suspension or elixir for oral administration, or wherein the composition is in the form of a sterile solution or suspension for parenteral administration or in a form suitable for preparing a sterile solution or suspension for parenteral administration; and/or
   (iv) wherein the composition is in unit dosage form comprising the zofenopril calcium crystalline form in an amount of from 1mg to 500mg.

8. A method of reducing blood pressure, comprising administering a therapeutically effective amount of the zofenopril calcium crystalline form according to claim 1 to a patient in need thereof.

9. A method according to claim 8, wherein the patient is a mammal.

10. A method according to claim 9, wherein the patient is a human.

11. A method according to claim 8, wherein the amount of the zofenopril calcium crystalline form administered is from 0.1mg to 100mg per kg per day.

12. A method of treating or preventing hypertension, myocardial infarction, acute myocardial infarction, heart failure or chronic heart failure, comprising administering a therapeutically or prophylactically effective amount of the zofenopril calcium crystalline form according to claim 1 to a patient in need thereof.

13. A method according to claim 12, wherein the patient is a mammal.

14. A method according to claim 13, wherein the patient is a human.

15. A method according to claim 12, wherein the amount of the zofenopril calcium crystalline form administered is from 0.1mg to 100mg per kg per day.

16. The zofenopril calcium crystalline form according to claim 1, wherein the zofenopril calcium comprises less than 3% of chemical impurities other than zofenopril calcium in other polymorphic or amorphous forms.

* * * * *